United States Patent [19]

Rodriguez

[11] Patent Number: 4,982,752
[45] Date of Patent: Jan. 8, 1991

[54] DENTAL FLOSS DEVICE

[76] Inventor: Nicolas Rodriguez, 1037 9th Ave., Barron, Wis. 54812

[21] Appl. No.: 388,630

[22] Filed: Aug. 2, 1989

[51] Int. Cl.[5] .............................................. A61C 15/00
[52] U.S. Cl. ..................................... 132/327; 132/324
[58] Field of Search ............... 132/323, 324, 325, 326, 132/327

[56] References Cited

U.S. PATENT DOCUMENTS

| | | | |
|---|---|---|---|
| 1,217,779 | 2/1917 | Kleckner | 132/325 |
| 1,815,408 | 7/1931 | Jordan | 132/323 |
| 2,444,697 | 7/1948 | Freyre | 132/92 |
| 2,451,181 | 10/1948 | Swartzman | 132/92 |
| 3,672,377 | 6/1972 | Greenacre | 132/92 |
| 3,882,879 | 5/1975 | Lucas | 132/92 |
| 3,910,294 | 10/1975 | Reed | 132/91 |
| 4,004,599 | 1/1977 | Rosenfeld | 132/92 |
| 4,026,308 | 5/1977 | Krivit | 132/91 |
| 4,192,330 | 3/1980 | Johnson | 132/323 |
| 4,427,018 | 1/1984 | Lagace | 132/91 |
| 4,706,694 | 11/1987 | Lambert | 132/92 |
| 4,736,757 | 4/1988 | Badoux | 132/91 |
| 4,738,271 | 4/1988 | Bianco | 132/92 |

*Primary Examiner*—Gene Mancene
*Assistant Examiner*—Michael Lynch
*Attorney, Agent, or Firm*—Merchant, Gould, Smith, Edell, Welter & Schmidt

[57] ABSTRACT

A dental floss holder includes a pair of elongated arm members (11), including cross member (14) located between said arm members (11). The arm members (11) are attached at first ends (12) and have floss holding slits (23) at second ends (13). The second ends may be squeezed toward one another to fasten the floss (15). The resiliency of the arm members (11) tautens the floss (15) upon the second ends (13) being released. As the floss (15) stretches during use, the arm members (11) may be squeezed toward one another causing the second ends (13) to pivot about the cross member (14), thereby restoring the floss (15) to its taut state.

9 Claims, 1 Drawing Sheet

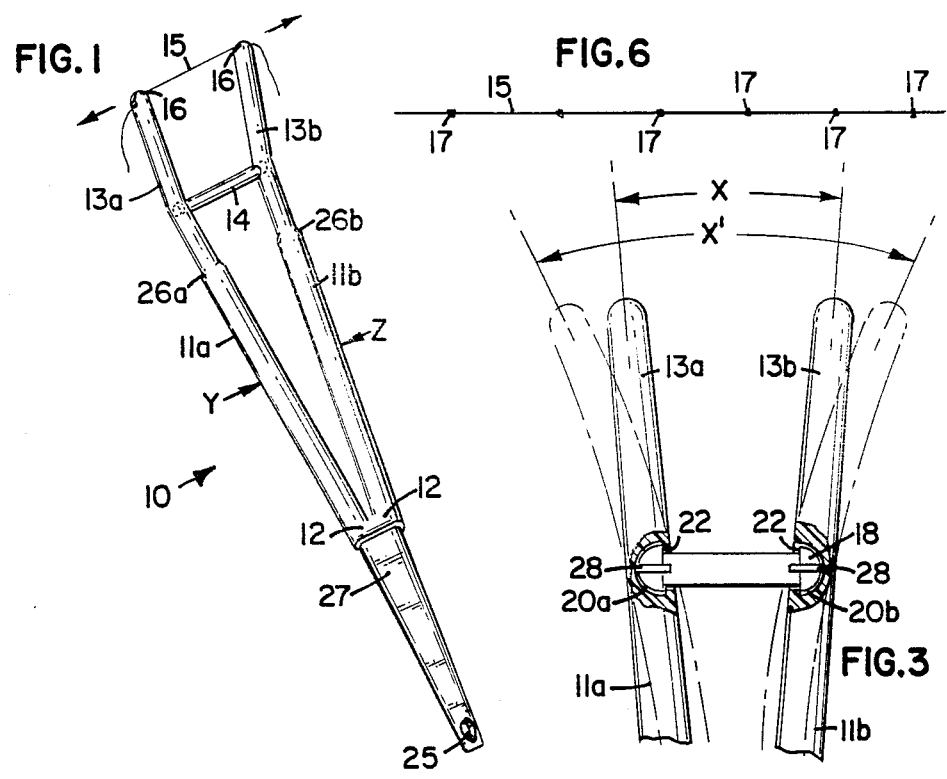
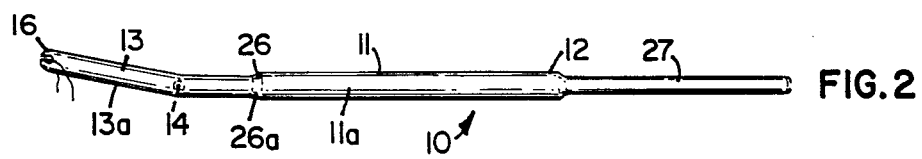
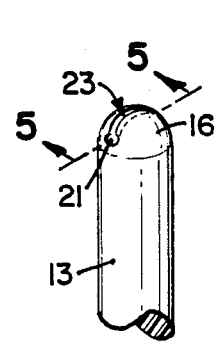
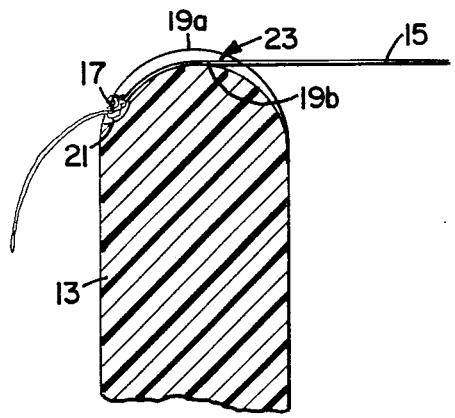

DENTAL FLOSS DEVICE

FIELD OF THE INVENTION

This invention relates generally to an oral hygiene apparatus, and more specifically to a dental flossing device for continuously holding floss tautly enabling use of the floss to clean interdental spaces.

BACKGROUND OF THE INVENTION

Various dental floss holders have previously been described wherein a length of dental floss is held under tension. For instance, in U.S. Pat. Nos. 4,736,757, 4,427,018, 2,444,697, and 1,815,408 opposing resilient arms are arranged such that the arms are moved toward one another when the floss is inserted. Subsequent to inserting the floss, the arms are released. Due to the resiliency of the arms, the arms tend to move apart from one another to their original position, thereby initially tensioning the floss.

Another device disclosed in U.S. Pat. No. 1,217,779 is adapted to hold floss under tension by using a retaining bar which spaces two opposed floss holding arms. The opposing arms have slits at their ends to receive the floss and the arms taper at the floss holding ends. Movement of the retaining bar toward the tips allows the arms to be compressed, providing relative movement toward one another. A length of floss is then inserted through the slits. By moving the bar away from the end, the arms move apart, thus resulting in the tensioning of the length of floss therebetween.

Each of the above described devices, however, has a similar drawback. The drawback relates to the stretching of floss during use. As the floss stretches, the devices are not capable of providing further tensioning of the floss beyond the normal original position of the arms.

One device, disclosed in U.S. Pat. No. 3,910,294, enables a continuous adjustment of the floss tension, but does so at the expense of a complex series of axes and the manual adjustment of a "tension adjusting lever." Adjustment of the lever pulls on the floss to create greater tension. Therefore, a second hand may be required by the operator to adjust the tension.

Therefore, there exists a need to develop a simple dental floss device which is capable of providing a continuous tensioning force to a length of floss as the length of floss stretches during use.

SUMMARY OF THE INVENTION

A preferred embodiment of an apparatus constructed according to the principles of the present invention includes a dental floss holding device which provides for maintaining a greater degree of tautness in the floss as the floss is stretched during use. In a preferred embodiment, a cross member is mounted between oppositely disposed arm members, the cross member providing a pivot point about which the arm members may pivot. The arm members are preferably connected at a first end and include floss holding means at a second end.

Prior to insertion of the floss in the floss holding means, the arm members are urged together by compressing the second ends toward one another. The floss is then inserted while the arm members are in this compressed state. When the second ends are released with the floss in place, preferably, the natural resiliency of the arm members urge the arm members away from one another thereby holding the floss tautly This position defines a first operative state. During use, the user may apply an inward force by squeezing at a middle portion of the arm member. By inward force, what is meant is a force applied to each of the arm members which is directed approximately toward the other arm member. The middle portion is defined as a portion located between the connected first end of the arm members and the cross member. The application of the force thereby pivots the arm members about the cross member. This forces the second ends of the arm members apart relative to one another, providing for further floss tautening. This position defines a variable second operative state.

Therefore, according to one aspect of the invention there is provided a dental flossing device of the type wherein floss is held between opposing members, comprising:

(a) two resilient elongate members each of said elongate members having a first and a second end, said elongate members cooperatively attached at said first end;

(b) cross member means, cooperatively attached to said elongate members between said first and second ends, for joining said elongate members, whereby an inward force applied to said elongate members between said first end and said cross member means causes relative movement of said second ends of said elongate members away from one another; and (c) tip means, cooperatively connected to said second ends of said elongate members, for securing the floss to said elongate members, whereby said floss may be tautly maintained between said elongate members by the application of said force.

These and other features and advantages which characterize the invention are pointed out with particularity in the claims annexed hereto and forming a part hereof. However, for a better understanding of the invention, its advantages and objectives obtained by its use, reference should be had to the following detailed description and the accompanying drawings in which there is illustrated and described a preferred embodiment of the invention.

BRIEF DESCRIPTION OF THE DRAWINGS

Referring the drawings, wherein like numbers represent like parts throughout the several views:

FIG. 1 is a perspective view of a preferred embodiment of a floss holding device constructed according to the principles of the present invention;

FIG. 2 is a side view of the device illustrated in FIG. 1;

FIG. 3 is a top view of a portion of the device illustrated in FIG. 1, with a second operative state illustrated in phantom line;

FIG. 4 is a perspective view of a second end of one of the arm members 11 of the device of FIG. 1;

FIG. 5 is a cross sectional view of the second end of FIG. 4 taken through line 5—5 of FIG. 4; and FIG. 6 is a preferred embodiment floss utilized in the floss holding device of FIG. 1.

DETAILED DESCRIPTION

The principles of this invention apply particularly well to its application to an interdental flossing device, for simplicity hereinafter referred to as the flossing device. An example of a preferred embodiment flossing device constructed according to the principles of the present invention is illustrated in FIG. 1. The flossing device is shown generally at 10.

Referring to FIG. 1, flossing device 10 includes arm or elongate members 11a and 11b which may be formed so as to be joined integrally proximate first ends 12. Alternatively, arm members 11a and 11b may be cooperatively connected at first ends 12 without being made integral to one another. Arm members 11a, 11b extend obliquely from one another, with the connection of first ends 12 forming an apex 27.

Formed within the arm members 11a, 11b are voids 20a, 20b (best seen in FIG. 3) into which cross member 14 is cooperatively inserted. Cross member 14 will be described further below. At a second end 13 of arm members 11a, 11b floss holding means 16 are provided which will also be described further below.

Arm members 11 are preferably made of a resilient plastic such as polyethylene, polypropylene, or high impact polystyrene, among others. However, as will become apparent to those skilled in the art, any materials having the characteristic of yielding to the requisite forces without breaking and tending to return to its original shape upon removal of the force may also be utilized. The arm members return to their original orientation or position subsequent to applying and releasing a force on the arm members 11 (either relatively toward or away from one another) A more thorough discussion of the application of a force to the arm members 11 and the operation of flossing device 10 will be deferred pending a more thorough discussion of the component parts of the preferred embodiment flossing device 10.

Arm members 11 are round from the apex 27 to second ends 13. The flossing device 10 tapers at tapered sections 26a, 26b. The connected apex portion 27 is flat in shape. Further, the arm members 11 are preferably shaped, arranged and configured so as to be convenient to the user. Here, arm members 11 are provided with a non-slip surface by providing slight grooves etched into the surface of the arm members 11. The grooves run parallel with one another along the longitudinal axis of arm members 11. The groves extend from first end 12 to tapered section 26. Such configuration aids the user when the flossing device 10 is being manually adjusted in the user's hand during operation.

To further enable ease of use of flossing device 10, second ends 13 are angled slightly out of the plane formed by arm members 11a, 11b. This angle occurs proximate the location of cross member 14. This angle promotes reaching into the user's interdental spaces.

Hole 25 is formed through the apex portion 27 of first ends 12 to provide means for hanging flossing device 10. A hook or other storage device may be inserted through hole 25 when flossing device 10 is not in operation.

Referring next to FIG. 3, the cooperative arrangement between cross member 14 and arm members 11 will be described. As illustrated, voids 20a and 20b are formed within arm members 11a and 11b respectively to provide for a cooperative engagement with cross member 14. Although preferred, such engagement is illustrative only and is a matter of design choice. Those skilled in the art will recognize that, cross member 14 may also be made integral with, or otherwise attached to, arm members 11.

Cross member 14 is located approximately two thirds of the distance from first ends 12 to second ends 13.

Retaining head members 18 are located on either end of cross member 14. The retaining head members 18 are approximately hemispherical in shape and are slotted 28 so that the head 18 may compress slightly when inserted into the void 20 through shoulder 22. The head 18 expands back to its original shape after insertion into void 20, thereby "locking" itself within void 20 and against shoulder 22. In essence, head members 18 are "snapped" into voids 20 to lock arm members 11a, 11b into a fixed spacial position relative to one another at that point where cross member 14 connects arm members 11a, 11b together. A small amount of movement of arm members 11a, 11b, relative to one another, may be afforded by properly arranging and configuring voids 20, shoulders 22 and retaining head members 18. The movement allows the necessary pivoting of arm members 11 about cross member 14. As noted, each head member 18 abuts shoulders 22 of the elongate members 11 such that the cross member 14 cannot be readily removed from arm members 11a, 11b once inserted.

With cross member 14 in position, and arm members 11 cooperatively attached at their first end, then the application of a force to the arm members 11a, 11b, between the first ends 12 and the cross member 14, will cause the second ends 13a, 13b of the elongate members 11 to move relative to one another. The movement of second ends 13 toward and away from one another occurs about the pivot point established by cross member 14. As illustrated in FIGS. 1 and 3, prior to the application of an inward force on elongate members 11 (and without floss 15 inserted), there is a distance x between the second ends 13 of elongate members 11. This position defines a non-operative state. Upon application of a force to elongate members 11 between first end 12 and cross member 14, second ends 13 move to a distance x'. The applied force, preferably occurs proximate points y and z (FIG. 1). However, those skilled in the art will recognize that the force may be applied at any point between the apex 27 of first ends 12 and cross member 14.

Turning now to the floss retaining means 16, best seen in FIGS. 4 and 5, it may be seen that, preferably, floss retaining means 16 are fabricated internally with second ends 13. Floss retaining means 16 are generally hemispherical with a guide slit 23 cut through floss retaining means 16 diameter. The first portion of guide slit 23 is rounded to form a hole 21. The hole 21 comprises that portion of floss retaining means 16 into which the knots 17 of floss 15 (described below) are inserted. The guide slit 23 tapers from the hole 21 to a slit which extends to the opposite side of floss retaining means 16. The guide slits 23 need only be tapered between round hole portion 21 and slit portion so as to retain the knot 17 within hole 21. The guide slit 23 is arranged and configured such that the knot 17 cannot readily be moved or pulled into the slit portion of guide slit 23.

The guide slit 23 is cut from the circumference 19a of floss retaining means 16 to a depth of 19b, therefore, the slit is not a true diameter cut, however, those skilled in the art will recognize that the depth of cut is a design choice. The depth of guide slit 23 allows the floss 15 to completely reside within guide slit 23 during operation. Use of floss 15 with knots 17 is a matter of design choice. Those skilled in the art will recognize that other types of floss could be used with floss securing means known in the art.

Referring next to FIG. 6, there is illustrated a preferred floss 15 to be utilized in flossing device 10. Floss 15 is illustrated as being of a typical style of floss, which is well known in the art and so will not be described further herein. However, such floss includes knots 17 tied at predetermined length. Knots 17 are arranged and configured so as to slightly compress second ends 13 of arm members 11 when inserted into the floss holding means 16. Therefore, the first operative state of flossing device 10 will maintain the floss 15 tautly between the second ends 13. As the floss stretches, the second ends 13 may be moved further apart first by the resilient force of arm members 11 and next by application of a force to arm members 11a, 11b as noted above.

In operation, first, arm members 11 are squeezed toward one another at their second ends 13. This portion defines a floss insertion state. Floss 15 is inserted by inserting a knot 17 within hole area 21 and extending the floss 15 through guide slit 23. The process is then repeated on the other second end 13. Second ends 13 are then released with the natural resiliency of arm members 11 causing a tautening of the floss 15 between the second ends 13 of arm members 11. The operator may then utilize the floss 15 by gripping the arm members 11. This position defines a first operative state.

As the floss stretches during interdental cleansing or the like, the operator merely squeezes the arm members 11 toward one another between the first ends 12 and the cross member 14, to tighten the floss 15. The application of this inward force causes the second ends 13 to move away from one another, thereby further tensioning the floss 15. Dependent upon the actual force applied, a variable second operative state is defined as the second ends 13 are forced away from one another. In this manner, the floss 15 is easier to use and requires less frequent changing.

It is to be understood that even though numerous characteristics and advantages of the present invention have been set forth in the foregoing description, together with details of the structure and function of the invention, the disclosure is illustrative only. Other modifications and alterations are well within the knowledge of those skilled in the art and are to be included within the broad general meaning of the terms in which the appended claims are expressed.

I claim:

1. A dental flossing device of the type wherein floss is held between opposing members comprising:
   (a) two resilient elongate members each of said elongate members having a first and a second end, said elongate members cooperatively attached at said first end;
   (b) cross member means, cooperatively attached to said elongate members between said first and second ends, for joining said elongate members, whereby an inward force applied to said elongate members between said first end and said cross member means causes relative movement of said second ends of said elongate members away from one another and wherein said elongate members pivot about said cross member means and the pivoting action is not restricted by said cross member means, and wherein voids are formed within said elongate members and said cross member means includes head retaining means which cooperatively engage with said voids; and
   (c) tip means, cooperatively connected to said second ends of said elongate members, for securing the floss to said elongate members, whereby said floss may be tautly maintained between said elongate members by the application of said force.

2. A dental flossing device for holding floss, of the type having knots tied at intervals, comprising:
   (a) at least two resilient arm members having a first end and a second end, said arm members cooperatively connected at said first end, said arm members having voids formed therein;
   (b) a cross member, pivotally connected to said arm members, located between said arm members so as to provide a pivot point about which the second ends of said arm members pivot upon the application of a force to said arm members, wherein said arm members are not restricted from pivoting by said cross member, said cross member including head retaining members which cooperatively engage with said voids; and
   (c) floss holding means cooperatively connected to said second ends, for securing said floss tautly between said arm members, wherein said second ends may be moved toward one another to secure the floss in a first operative position and said arm members may be moved toward one another by application of an inward force to pivot said second ends away from each other to a second operative position.

3. The flossing device as recited in claim 2, wherein said floss holding means comprises a slit located transversely through said elongate member and a hole formed at one end of said slit, whereby the slit guides the floss between said elongate members and said hole provides for retaining the knots in the floss.

4. The device as recited in claim 2, wherein said pivoting action of said second ends provides a continuous tensioning force to the length of floss.

5. The device as recited in claim 4, wherein said arm members are round from said first end to said second end.

6. The device as recited in claim 2, wherein each of said arm members form an angle, wherein said arm members proximate said first end define a plane and said second ends of said arm members extend out of said plane.

7. The device as recited in claim 6, wherein said first ends are integrally formed and form an apex from which said arm members extend obliquely.

8. The device as recited in claim 7, wherein a hole is formed through said apex.

9. The device as recited in claim 8, wherein grooves are etched in said arm members along said arm members longitudinal axis to provide for a positive gripping surface for an operator of the device.

* * * * *